(12) United States Patent
Longchamp et al.

(10) Patent No.: US 10,515,791 B2
(45) Date of Patent: Dec. 24, 2019

(54) METHOD AND APPARATUS FOR IMAGING SINGLE MOLECULES

(71) Applicant: UNIVERSITAET ZUERICH, Zurich (CH)

(72) Inventors: Jean-Nicolas Longchamp, Glattpark (CH); Hans-Werner Fink, Zurich (CH); Conrad Escher, Zurich (CH)

(73) Assignee: UNIVERSITAET ZUERICH, Zurich (CH)

( * ) Notice: Subject to any disclaimer, the term of this patent is extended or adjusted under 35 U.S.C. 154(b) by 0 days.

(21) Appl. No.: 16/068,672

(22) PCT Filed: Jun. 29, 2016

(86) PCT No.: PCT/EP2016/065222
§ 371 (c)(1),
(2) Date: Jul. 8, 2018

(87) PCT Pub. No.: WO2017/118494
PCT Pub. Date: Jul. 13, 2017

(65) Prior Publication Data
US 2019/0035616 A1 Jan. 31, 2019

(30) Foreign Application Priority Data

Jan. 8, 2016 (EP) .................................... 16150566

(51) Int. Cl.
*H01J 49/00* (2006.01)
*H01J 49/16* (2006.01)
(Continued)

(52) U.S. Cl.
CPC ........ *H01J 49/165* (2013.01); *G01N 23/2251* (2013.01); *H01J 37/26* (2013.01);
(Continued)

(58) Field of Classification Search
CPC .... H01J 49/00; H01J 49/0004; H01J 49/0027; H01J 49/0031; H01J 49/02; H01J 49/165;
(Continued)

(56) References Cited

U.S. PATENT DOCUMENTS

2004/0004183 A1* 1/2004 Grant .................. H01J 49/0409
250/281

FOREIGN PATENT DOCUMENTS

WO 2014064057 A2 5/2014

OTHER PUBLICATIONS

Jean-Nicolas Longchamp et al.: "How to Image a Single Protein", Dec. 31, 2015, pp. 1-12. (Year: 2015).*
(Continued)

*Primary Examiner* — Jason L McCormack
(74) *Attorney, Agent, or Firm* — Agris & Von Natzmer, LLP; Joyce Von Natzmer

(57) ABSTRACT

A method of imaging single molecules, comprises the steps of: a) providing an assembly comprising a carrier substrate having a substrate face with an aperture, the aperture being covered with a receiving layer attached to the substrate face, the receiving layer being substantially transparent for low-energy electrons with a kinetic energy of 5 to 1,000 eV; b) depositing single molecules onto said receiving layer by means of soft-landing electrospray ion deposition, whereby a single molecule loaded receiving layer is formed; c) acquiring an in-line low-energy electron transmission pattern of said single molecule loaded receiving layer; and d) applying a reconstruction procedure to said electron transmission pattern to obtain at least one image of a single molecule on said single molecule loaded receiving layer. The above steps a) to c) are conducted under vacuum conditions.

18 Claims, 5 Drawing Sheets

(51) Int. Cl.
*G01N 23/2251* (2018.01)
*H01J 37/26* (2006.01)
*H01J 49/04* (2006.01)
*H01J 49/40* (2006.01)

(52) U.S. Cl.
CPC .......... *H01J 49/0409* (2013.01); *H01J 49/40* (2013.01); *H01J 2237/2614* (2013.01)

(58) Field of Classification Search
CPC .......... H01J 37/00; H01J 37/26; H01J 37/261; H01J 37/02; H01J 2237/2802
USPC .......................... 250/281, 282, 306, 307, 311
See application file for complete search history.

(56) References Cited

OTHER PUBLICATIONS

Jean-Nicolas Longchamp et al.: "How to image a single protein", Dec. 31, 2015, pp. 1-12.
Jean-Nicolas Longchamp et al.: "Ultraclean freestanding graphene by platinum-metal catalysis", Journal of Vacuum Science & Technology B, vol. 31, No. 2, Mar. 1, 2013, pp. 20605-20605.
Tatiana Latychevskaia et al.: "Holography and coherent diffraction with low-energy electrons: A route towards structural biology at the single molecule level", Ultramicroscopy, vol. 159, Dec. 2, 2014, pp. 395-402.

* cited by examiner

METHOD AND APPARATUS FOR IMAGING SINGLE MOLECULES

CROSS-REFERENCE TO RELATED APPLICATIONS

This is the U.S. national stage of International application PCT/EP2016/065222, filed Jun. 29, 2016 designating the United States and claiming priority to EP 16150566.4, filed Jan. 8, 2016.

FIELD OF THE INVENTION

The present invention relates to a method and an apparatus for imaging single molecules, particularly single protein molecules.

BACKGROUND OF THE INVENTION

Most of the protein structural information available today has been obtained from either X-ray crystallography experiments or cryo-electron microscopy investigations by means of averaging over many molecules assembled into a crystal or over a large ensemble selected from low signal-to-noise ratio electron micrographs respectively[10]. Despite the impressive amount of available data, a strong desire for acquiring structural data from just one individual molecule is emerging for good reasons. Most of the biologically relevant molecules exhibit different conformations; the associated structural details however, remain undiscovered when averaging is involved. Moreover, a large subset of the entirety of proteins, in particular out of the important category of membrane proteins, does not crystallize at all. If just one individual protein or protein complex can be analysed in sufficient detail, also those objects become finally accessible.

For a meaningful contribution to structural biology, a tool for single molecule imaging has to allow for observing an individual protein long enough to acquire a sufficient amount of data for revealing its structure, ideally without destroying it. The strong inelastic scattering cross-section for both, X-rays and high-energy electrons as employed in the state-of-the-art aberration corrected TEMs, inhibits accumulation of sufficient elastic scattering events required in order to reveal high-resolution reconstruction of just one molecule. Future X-ray Free Electron Lasers (XFELs) with drastically enhanced brightness and reduced pulse duration might eventually achieve the goal of single molecule imaging. Yet, the current and foreseeable state-of-the-art in XFEL performance still requires averaging over at least 1 million molecules[1,11-13].

Apart from protein molecules, there are also many other types of other molecules for which single molecule imaging would be desirable. These comprise molecules with a variety of molecular sizes.

In view of the above, it is an object of the present invention to provide a method and an apparatus for imaging single molecules.

SUMMARY OF THE INVENTION

It has now been found that the above object can be achieved by means of a method as defined in claim 1.

Therefore, according to one aspect of the invention, a method of imaging single molecules comprises the steps of:
a) providing an assembly comprising a carrier substrate having a substrate face with an aperture, the aperture being covered with a receiving layer attached to the substrate face, the receiving layer being substantially transparent for low-energy electrons with a kinetic energy of 5 to 1,000 eV;
b) depositing single molecules onto said receiving layer by means of softlanding electrospray ion deposition, whereby a single molecule loaded receiving layer is formed;
c) acquiring an in-line low-energy electron transmission pattern of said single molecule loaded receiving layer; and
d) applying a reconstruction procedure to said electron transmission pattern to obtain at least one image of a single molecule on said single molecule loaded receiving layer;
the above steps a) to c) being conducted under vacuum conditions.

According to another aspect of the invention, an apparatus for carrying out the method for imaging single molecules comprises:
a) a vacuum chamber containing a carrier substrate having a substrate face with an aperture, the aperture being covered with a receiving layer attached to the substrate face, the receiving layer being substantially transparent for low-energy electrons with a kinetic energy of 5 to 1,000 eV;
b) means for depositing single molecules onto said receiving layer by means of soft-landing electrospray ion deposition to form a single molecule loaded receiving layer; and
c) means for acquiring an in-line low-energy electron transmission pattern of said single molecule loaded receiving layer.

In the present context, the term "low-energy electrons" shall be understood to refer to electrons having a kinetic energy in the range of 5 to 1,000 eV with respect to the receiving layer onto which they are directed.

In principle, the method of the present invention can be applied to a large variety of molecules ranging from small inorganic or organic molecules all the way to very large biomolecules. It is also applicable to assemblies of molecules such as dimers, oligomers and clusters.

It will be understood that in case of very small, comparatively volatile molecules such as triatomics oder even diatomics, it may be necessary to cool the receiving layer to temperatures well below ambient temperature in order to achieve a sufficiently stable arrangement of single molecule on the receiving layer.

The term "soft-landing electrospray ion deposition" shall be understood as an implementation of the generally known methodology of electrospray ion deposition wherein "soft-landing" shall refer to a deposition conducted with an ion impact energy that is small enough to avoid any undesired effects. The corresponding energy threshold depends on the particular application. In many cases the impact energy shall be low enough to avoid dissociation of molecular bonds. Clearly, however, the study of weakly bound molecular assemblies will require particularly soft deposition conditions.

Advantageous embodiments are defined in the dependent claims and in the description further below.

According to one embodiment (claims 2 and 10), the deposition of single molecules comprises ionization of single molecules to form single molecular ions, electrostatic extraction and mass filtering of said single molecular ions and electrostatic guidance of mass filtered single molecular ions onto said receiving layer.

According to one embodiment (claims 3 and 11), the single molecules are protein molecules.

According to an advantageous embodiment (claims 4 and 12), the receiving layer is a graphene monolayer. Ultraclean freestanding graphene can be prepared by the Pt-metal catalysis method described in detail elsewhere[6] (see also: WO 2014/064057 A2).

In principle, various types of electron transmission pattern can be used to obtain the desired information of the single molecules of interest. For example, one can use a low-energy electron diffraction pattern technique. According to an advantageous embodiment (claims 5 and 9), the electron transmission pattern is a hologram.

According to a further favorable embodiment (claims 6 and 13), the substrate face consists of a platinum metal selected from the group consisting of Pt, Pd and Rh, preferably Pt.

According to an advantageous embodiment, the apparatus of the present invention further comprises means for applying a reconstruction procedure to said electron transmission pattern to obtain at least one image of a single molecule on said single molecule loaded receiving layer.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein are shown.

DETAILED DESCRIPTION OF THE INVENTION

Experimental Studies

Ultraclean freestanding graphene was prepared by the Pt-metal catalysis method described in detail elsewhere[6]. Prior to the transfer of the ultraclean substrate from the UHV chamber of the low-energy electron holographic microscope to the UHV chamber of the ES-IBD device, the cleanliness of the substrate is characterized and reference images are recorded for comparing the very same region of freestanding graphene before and after protein deposition.

During the whole experimental workflow, the samples are kept under strict UHV conditions with the help of a UHV suitcase for transfer between the two experimental chambers.

Figure 1:
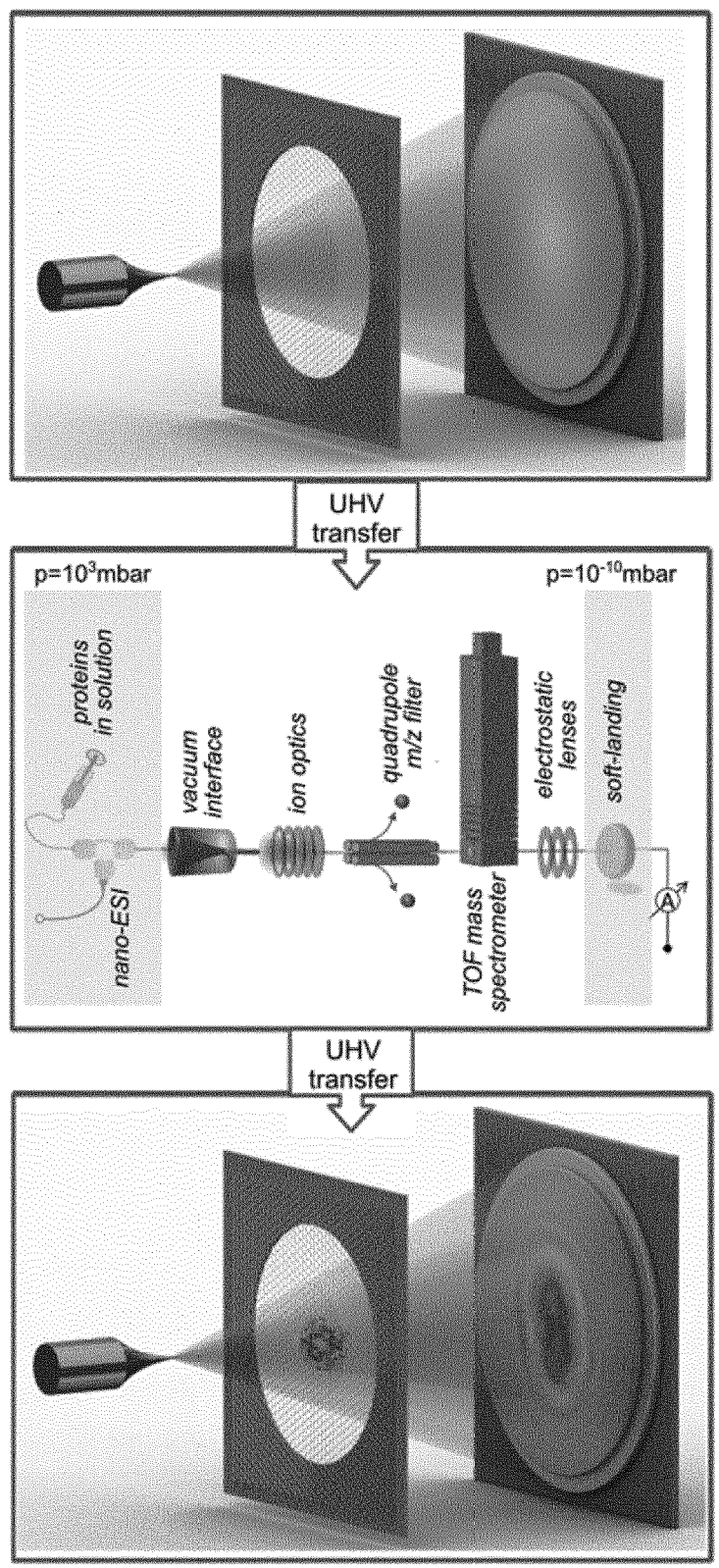
FIG. 1: Schematic workflow for imaging a single protein. From top to bottom: Preparation and characterisation of ultraclean freestanding graphene. Deposition of proteins onto freestanding graphene in a m/z filtered ES-IBD system. Imaging of the proteins within the previously characterised region by means of low-energy electron holography. During the whole experimental workflow, the sample is kept under strict UHV conditions with the help of a UHV suitcase for the transfer between the two experimental chambers (see Supplementary Information for more details).
Figure 2:
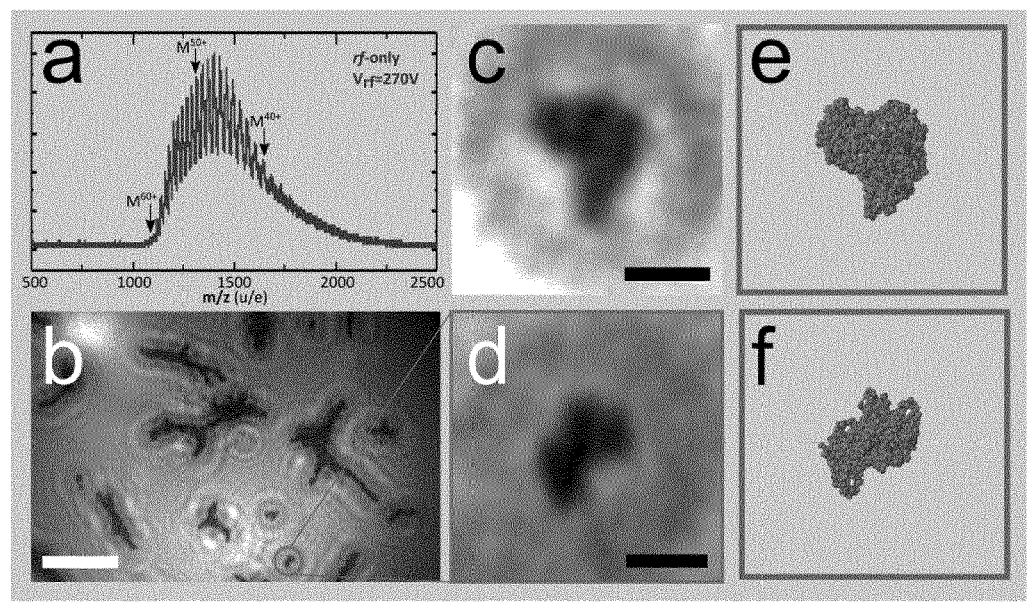
FIG. 2: Images of individual BSA proteins deposited onto freestanding graphene. a, Mass spectrum of the BSA ion beam. Ion beams of mainly unfolded BSA (Sigma A4919) were prepared by electrospraying solutions of 0.4 mg/mL BSA dissolved in a 1:1 mixture of water and ethanol to which 2% formic acid is added. At a flow rate of 30 μL/hr, an ion current of 2 nA is measured at the TOF-MS. The mass spectrum above 1000 u/e shows the characteristic peak group of multiply charged proteins (z=+35 . . . +60). The low m/z range (<1000 u/e) as well as the high m/z range (>2000 u/e) is free of any peaks indicating a pure beam free of contamination and unspecific agglomerations. b, Survey image of the deposited high-charge state BSA proteins on graphene. As expected from the mass spectrum the vast majority of proteins are in an unfolded state. Two high magnification images of BSA in a folded structure are presented in c and d. The scale bars correspond to 50 nm in b and 5 nm in c and d. The atomic model of BSA from the protein data bank (pdb id: 3V03) in the corresponding orientations is displayed in e and f for comparison.

Details of the ES-IBD procedure and of the low-energy electron holography experimental scheme are described in the supplementary information The workflow for imaging a single protein involves several steps as illustrated in FIG. 1. An ultraclean freestanding graphene sample is prepared using the recently developed platinum metal catalysis method[6] and characterized in the low-energy electron holographic microscope (FIG. 1 top). Such sample is subsequently transferred to an ES-IBD system (FIG. 1 middle) under permanent UHV conditions by means of a UHV suitcase operating in the $10^{-11}$ mbar regime (see Supplementary Information for more details). Native cytochrome C (CytC), and haemoglobin (HG) ion beams are generated by electrospray ionization and mass filtering. For CytC the charge states $z=5-7$ are selected[15]. In the case of HG the charge states $z=16$ or $z=17$ of the intact complex are known to be of native conformation[16] and hence the corresponding m/z region is selected (the corresponding mass spectra are displayed in the Supplementary Information). In a third experiment, bovine serum albumin (BSA) in the high-charge states $z=35-60$ is chosen for deposition (see FIG. 2). In all three cases, the ions land with a kinetic energy of 2-5 eV per charge[14] on ultraclean freestanding graphene covering 500×500 $nm^2$ apertures milled in a 100 nm thick SiN membrane[6].

After deposition, the samples are transferred again under preserved UHV conditions from the ES-IBD system back to the low-energy electron holographic microscope, where low-energy electron holograms of individual proteins are recorded[13]. In this experimental scheme inspired by Dennis Gabor's original idea of holography, the samples are presented to a highly coherent beam of low-energy electrons generated by an atomically sharp field emitter tip placed as close as 100 nm in front of the sample (FIG. 1 bottom). The interference pattern formed by the scattered and the unscattered electron waves, the so-called hologram, is recorded at a several centimetres distant electron detector (for more details see supplementary information). Subsequent numerical hologram reconstruction involving back propagation of the wave front from the hologram to the sample plane[17-19] finally reveals the protein structure.

Figure 3:
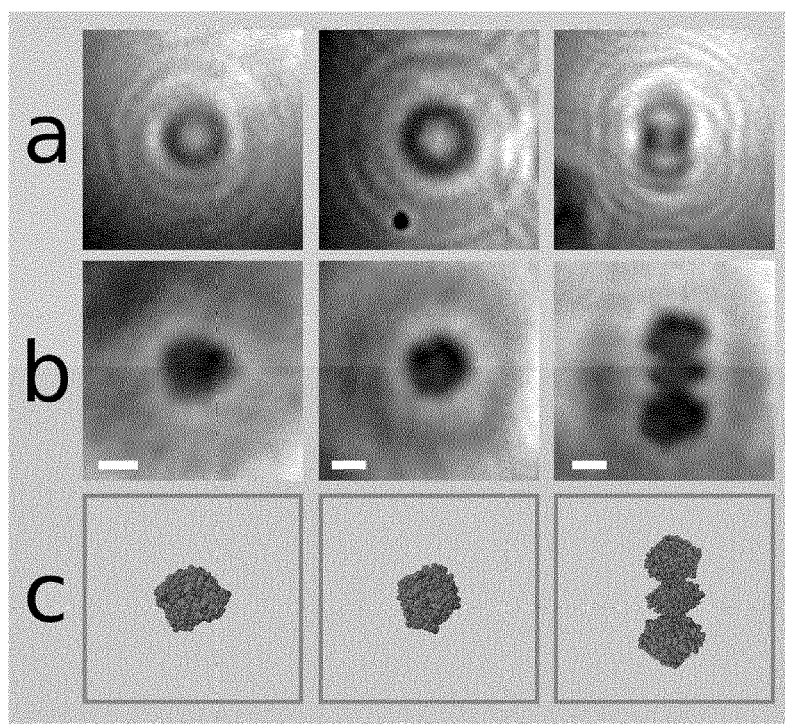
FIG. 3: Low-energy electron holograms of cytochrome C and their reconstructions. a, Three holograms of CytC recorded at kinetic electron energies of 142 eV (left), 132 eV (middle), and 117 eV (right). b, Numerical reconstructions showing the protein in different orientations on graphene. The scale bars correspond to 2 nm. c, Suggestions for possible orientations based on the averaged protein structure derived from X-ray crystallography data and documented in the protein data bank (pdb id:1 HRC).
Figure 4:
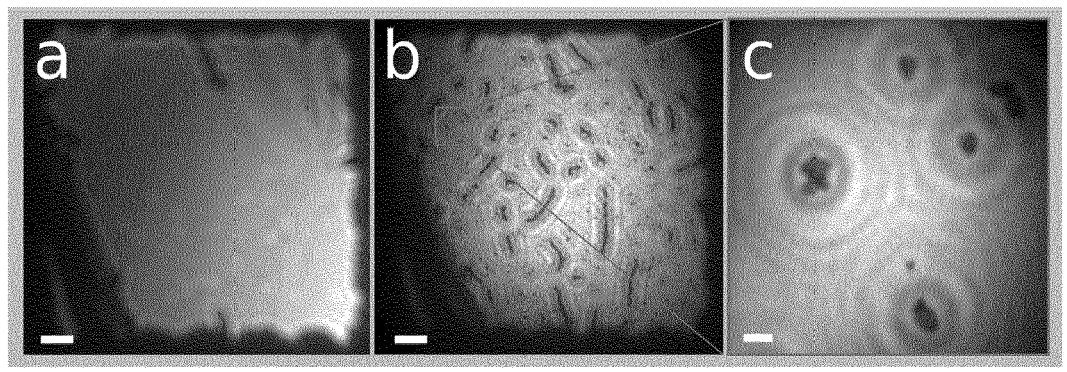
FIG. 4: Freestanding graphene before (a) and after (b) the deposition of pA/h native CytC. In b individual globular objects of a size of 2-5 nm or agglomerates thereof are observed. Such agglomeration has previously been observed on a Au(111) surface after deposition of native CytC in low charge states[14]. c, After moving the electron point source closer to the globular objects, their dimensions can be measured and correspond to the size of individual folded CytC molecules. The scale bars correspond to 50 nm in a and b and to 5 nm in c.

Holograms of individual CytC proteins and their respective reconstructions are presented in FIG. 3(a-b). Survey images of freestanding graphene before and after deposition of CytC is presented in FIG. 4. The shapes of the imaged proteins are compared with the structural data information obtained from X-ray crystallography investigations and available from the protein data bank (pdb id: 1HRC). The overall size of the imaged CytC corresponds to the expected dimensions and the low-energy electron images can be associated with proteins in several distinct orientations. The resolution in the electron images is sufficient to identify individual CytC as well as agglomerates thereof (FIG. 3b). As demonstrated previously with DNA[8], no sign of decomposition of the protein during electron exposure is observed.

Figure 5:
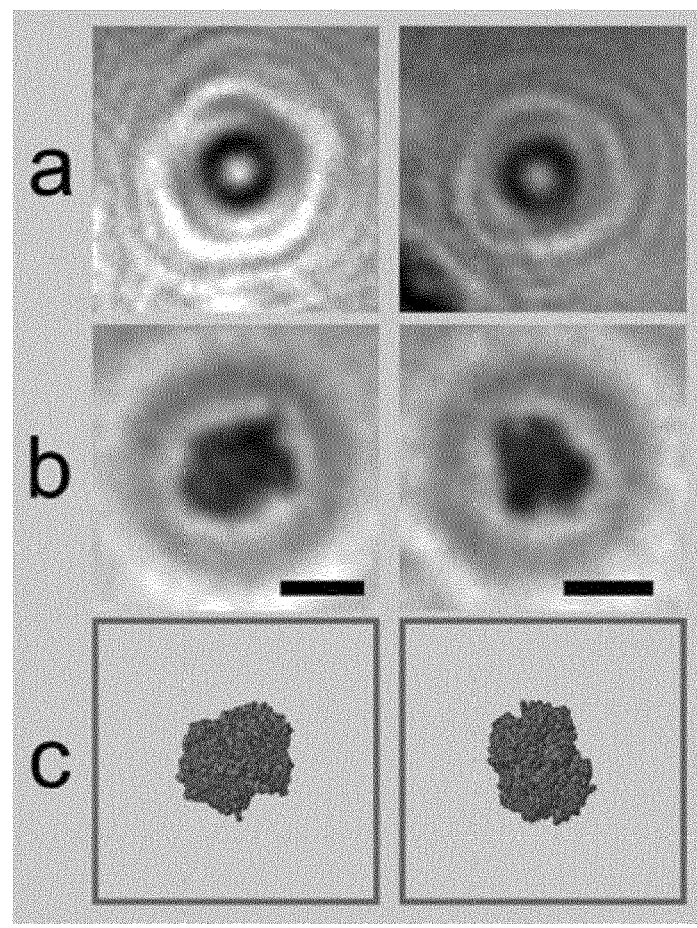
FIG. 5: Low-energy electron holograms of two individual haemoglobin and their reconstructions. a, Two holograms of haemoglobin recorded at kinetic electron energies of 71 eV (left) and 69 eV (right) respectively. b, Numerical reconstructions showing the protein complex in two different orientations on graphene. The scale bars correspond to 5 nm. The diffuse rings around the object are due to the presence of the out-of-focus twin image inherent to in-line holography. c, Suggestions for possible orientations based on the averaged protein structure derived from X-ray crystallography data and documented in the protein data bank (pdb id: 2QSS).

From the data displayed in the right column of FIG. 3, it remains unsettled whether the agglomerate formed by several CytC has assembled prior or past deposition. On the other hand, in FIG. 5 two holograms and their respective reconstructions of individual haemoglobin are presented demonstrating that with our method it is not only possible to image individual proteins but also to deposit and image entire biologically relevant protein complexes. As apparent from the high contrast images of individual haemoglobin, not just the globular structure with the correct overall dimensions of the protein complex is revealed, but also details of its shape in different orientations. In FIG. 5(b right), structural features of 0.7-0.8 nm in size can clearly be identified and may serve as a rough resolution estimate for the low-energy electron images. In a hologram the spacing between consecutive interference fringes gradually decreases towards higher orders. Hence, high-order interference fringes and consequently high-resolution structural details are most susceptible to mechanical vibrations. The latter are currently limiting the resolution and intense efforts are ongoing to increase the mechanical stability of the low-energy electron holographic microscope in order to overcome this limitation and approach atomic resolution.

Figure 6:
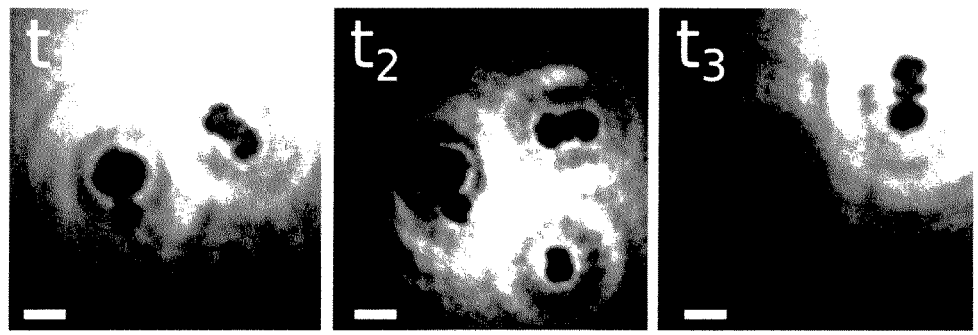
FIG. 6: Time evolution of the orientation of CytC complexes. The time lapse between subsequent observations amounts to 30 sec. From these images it is evident that at least some of the deposited proteins are mobile on freestanding graphene. Low-energy electron holography appears to be a method for also studying diffusion of proteins on surfaces. This observation suggests that a low-energy electron holographic microscope operating at cryogenic temperatures might be needed in order to fix the protein in space and attain atomic resolution. The scale bars correspond to 5 nm.

At this stage, the comparison with the protein data bank structure has the character of a control experiment. However, the future goal is to directly uncover the structure of unknown proteins and all their possible conformations that might differ in the position of a small number of atoms only. Nevertheless, on the road towards this ambition, additional fundamental questions remain to be addressed as for instance: the influence of the substrate, the possibility to add a hydration shell under UHV conditions, as well as issues related to transport, like diffusion of proteins and subsequent association into protein complexes. First observations of diffusion of folded proteins on freestanding graphene by means of low-energy electron holography are presented in FIG. 6 illustrating that our method described here is also capable of accessing dynamical processes.

To conclude, we have shown how to image a single protein by combining the ES-IBD technology with low-energy electron holography. This has led to the first tool ever for revealing structural details of native single proteins and protein complexes without destroying them. With the recent advances in electrospray ionization of large protein complexes[20] and in particular membrane proteins[21,22], even the structure of these biologically important but reluctant to readily crystallize entities will possibly become accessible in the near future.

While bare freestanding graphene has already been imaged with 2 Angstrom resolution by coherent diffraction with low-energy electrons[23], it is now a challenge of adopting the technologies described here for reaching atomic resolution in structural biology at the single protein level.

Supplementary Information

Electrospray Ion Beam Deposition (ES-IBD)

Soft-landing electrospray ion beam deposition takes place in a home-built instrument[4,5]. The ion beam is generated by a nano electrospray source with an optimized hydrodynamic behaviour[24] at a flow rate of 20-30 µL/h and an emitter voltage of approximately 3 kV. The positive ions enter the vacuum through a heated metal capillary and are collimated in an ion funnel and a collisional collimation quadrupole operated in rf-only mode. In the third pumping stage a mass filtering quadrupole selects the m/z region of interest, which is monitored by the time-of-flight mass spectrometer in the fourth pumping stage. Here, a retarding field energy analyser measures the kinetic energy of the ions. The beam is then guided by electrostatic lenses towards the target in the $6^{th}$ pumping stage being at $2×10^{-10}$ mbar, where the protein deposition takes place. To ensure gentle landing, the collision energy is controlled by applying a bias voltage to the target and hence reducing the kinetic energy of the protein ions.

Figure 7:
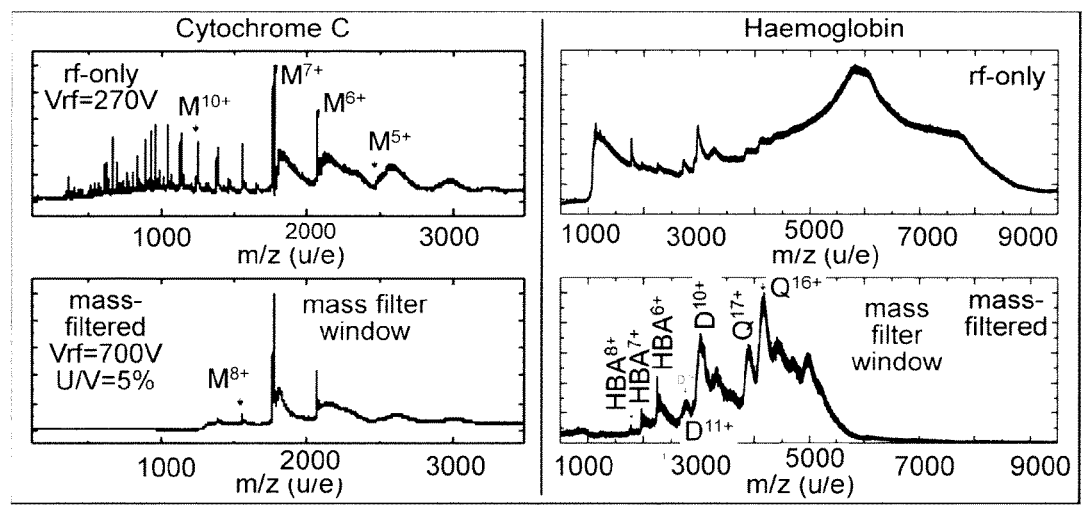
FIG. 7: Mass spectra of Cytochrome C (left) and Haemoglobin (right). Top: the m/z spectra before mass filtering are displayed. Bottom: the corresponding mass-filtered spectra.

To obtain ion beams of native CytC (bovine, Fluka 30398), a solution of 0.15 mg/mL was prepared in aqueous 50 mM ammonium acetate buffer. With a spray flow rate of 25 µL/hr, an ion current of 1.1 nA is detected at the TOF-MS. Unfiltered mass spectra (FIG. 7 left/top) show low charge states of +5 to +7, corresponding to folded CytC. At lower m/z values peaks corresponding to highly charged (z>+8) unfolded CytC and peaks that relate to fragments or contamination are found. Note that, due to the limited dynamic range of the TOF-MS, the detector amplification was set very high, such that the peaks of the native CytC are distorted. The m/z selective quadrupole was tuned to select a m/z-window from 1250 u/e to approximately 3500 u/e by setting a rf-amplitude of 700V with a differential dc-voltage of 5%. This results in a beam of predominantly native CytC (FIG. 7 left/bottom) from which unfolded proteins (low m/z) and undefined heavy aggregates (high m/z) are removed.

Haemoglobin (bovine, Sigma H2500) is a protein complex of four myoglobin subunits, two A and two B. Ion beams are generated from solutions of 0.3 mg/mL HG prepared in 50 mM ammonium acetate buffer. A current of 600 pA is detected at the TOF-MS. The mass spectrum is very complex and is resolved only partially due to the limited performance concerning resolution and dynamic range of the home-built linear TOF-MS. Nevertheless, a comparison with literature spectra allows identifying characteristic peaks (FIG. 7 right/bottom), which become more pronounced after removal of the unspecific agglomeration in the high m/z range (>5000 u/e) by mass filtering with the quadrupole. The beam transmitted for deposition contains native intact HG complexes ($Q^{17+}$, $Q^{16+}$) along with dimers (D) and monomers (HBA).

Low-Energy Electron Holography.

Figure 8:
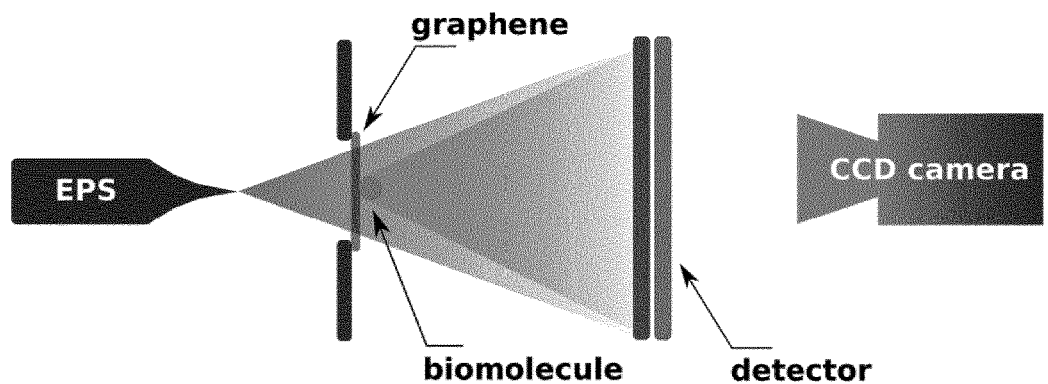
FIG. 8: UHV Vacuum Suitcase and its performance. a, Three-dimensional rendering of the transport suitcase enabling UHV transfer of ultraclean freestanding graphene between the low-energy electron microscope and the ES-IBD chamber. Low-energy electron projection images before (b) and after (c) a complete transfer and travel cycle without protein deposition. During the course of the transfer procedure between the two vacuum chambers no relevant contamination of the graphene built up.

In the low-energy electron holographic setup[3] ((FIG. 8), inspired by Dennis Gabor's original idea of in-line holography[25,26], a sharp (111)-oriented tungsten tip acts as electron point source (EPS) providing a divergent beam of highly coherent electrons[27,28]. The atomic sized electron field emitter can be brought as close as 100 nm to the sample with the help of a 3-axis nanopositioner. Part of the electron wave is elastically scattered off the object and hence is called the object wave, while the un-scattered part of the wave represents the reference wave. At a distant detector, the hologram, i.e. the pattern resulting from the interference of these two wave fronts is recorded. The magnification of the imaging system is given by the ratio between detector-to-source distance and sample-to-source distance and can be as high as $10^5$. A hologram, in contrast to a diffraction pattern, contains the phase information of the object wave, and the object structure can thus be reconstructed unambiguously. The numerical reconstruction from the hologram is essentially achieved by back propagation to the object plane, which corresponds to evaluating the Fresnel-Kirchhoff integral transformation[17-19].

UHV Transfer

A vacuum suitcase, FIG. 9(a) (Ferrovac GmbH, Zurich), is used to transfer samples between the two UHV based experiments, electron holography on the one side, and electrospray ion beam deposition on the other side.

The suitcase is equipped with a SAES getter/ion getter pump combination operated by a battery driven power supply. The pressure is kept below $2\times10^{-10}$ mbar at all times, except for the short duration of the transfer (1-2 minutes) where it rises into the $1\times10^{-9}$ mbar regime. The performance of this suitcase, originally developed for STM experiments is well known from various surface science studies[29,30].

Figure 9:
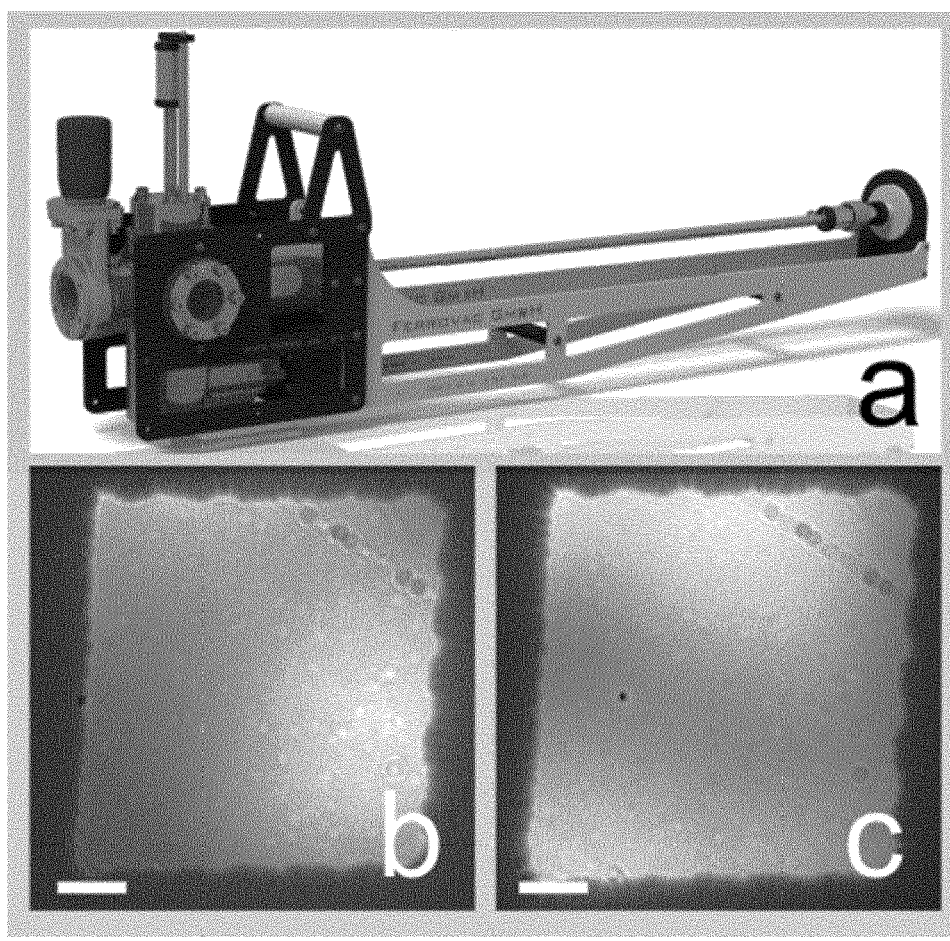
FIG. 9: UHV Vacuum Suitcase and its performance. a, Three-dimensional rendering of the transport suitcase enabling UHV transfer of ultraclean freestanding graphene between the low-energy electron microscope and the ES-IBD chamber. Low-energy electron projection images before (b) and after (c) a complete transfer and travel cycle without protein deposition. During the course of the transfer procedure between the two vacuum chambers no relevant contamination of the graphene built up.

Each instrument is equipped with a load-lock to which the suitcase can be attached. The load-lock is pumped by a turbo molecular pump supported by a cryogenic active charcoal trap at $LN_2$ temperature. A pressure in the $10^9$ mbar range is established within a few hours, ensuring a contamination-free transfer of the samples. FIG. 9 shows low-energy electron projection images of the very same freestanding graphene region before (b) and after (c) the transfer from the low-energy electron holographic microscope located in Zurich to the ES-IBD chamber in Stuttgart and back to the microscope in Zurich. No relevant sign of contamination due to transfer and transport is observed.

Concluding Remarks:

To achieve the goal of imaging single molecules, exemplified here for the case of single protein molecules, one needs to master and combine three requirements. At first, a method for isolating individual proteins for further inspection has to be at hand; quite the opposite to the current challenge of assembling proteins into a crystal for X-ray analysis[1,2]. Furthermore, technologies are required for keeping a single protein fixed in space long enough to accumulate sufficient structural information from a scattering experiment. Last but not least, gentle radiation with a wavelength small enough to uncover structural details while ensuring that radiation damage does not decompose the protein during observation as it is available by low-energy electron holography[3] is vital for imaging. Here we show that soft-landing electrospray beam deposition[4,5] allows for specific selection and sound deposition[5] of individual proteins and protein complexes onto ultraclean freestanding graphene[6] in an ultra-high vacuum environment. Due to the fact that graphene is transparent for low-energy electrons[7] and since the latter do not damage biological molecules[8,9], we were able to acquire high signal-to-noise ratio electron holograms of individual proteins (Cytochrome C and BSA) as well as of protein complexes (haemoglobin). The numerical hologram reconstructions reveal the overall shape of single proteins. With this, images of individual folded proteins and protein complexes, not being the result of an averaging process, have been obtained for the first time.

REFERENCES

1. Chapman, H. N. et al. Femtosecond X-ray protein nanocrystallography. *Nature* 470, 73-77 (2011).
2. Caleman, C. et al. On the feasibility of nanocrystal imaging using intense and ultrashort X-ray pulses. *ACS Nano* 5, 139-46 (2011).
3. Fink, H.-W., Stocker, W. & Schmid, H. Holography with low-energy electrons. *Phys. Rev. Lett.* 65, 1204-1206 (1990).
4. Rauschenbach, S. et al. Electrospray Ion Beam Deposition of Clusters and Biomolecules. *Small* 2, 540-547 (2006).
5. Rauschenbach, S. et al. Electrospray Ion Beam Deposition: Soft-Landing and Fragmentation of Functional Molecules at Solid Surfaces. *ACS Nano* 3, 2901-2910 (2009).
6. Longchamp, J.-N., Escher, C. & Fink, H.-W. Ultraclean freestanding graphene by platinum-metal catalysis. *J. Vac. Sci. Technol. B Microelectron. Nanom. Struct.* 31, 020605 (2013).
7. Longchamp, J.-N., Latychevskaia, T., Escher, C. & Fink, H.-W. Low-energy electron transmission imaging of clusters on free-standing graphene. *Appl. Phys. Lett.* 101, 113117 (2012).

8. Germann, M., Latychevskaia, T., Escher, C. & Fink, H.-W. Nondestructive imaging of individual biomolecules. *Phys. Rev. Lett.* 104, 095501 (2010).
9. Longchamp, J.-N., Latychevskaia, T., Escher, C. & Fink, H.-W. Non-destructive imaging of an individual protein. *Appl. Phys. Lett.* 101, 93701 (2012).
10. Callaway, E. The revolution will not be crystallized: a new method sweeps through structural biology. *Nature* 525, 172-174 (2015).
11. Neutze, R., Wouts, R., van der Spoel, D., Weckert, E. & Hajdu, J. Potential for biomolecular imaging with femtosecond X-ray pulses. *Nature* 406, 752-757 (2000).
12. Miao, J. W., Sandberg, R. L. & Song, C. Y. Coherent X-ray diffraction imaging. *Ieee J. Sel. Top. Quantum Electron.* 18, 399-410 (2012).
13. Miao, J. W., Hodgson, K. O. & Sayre, D. An approach to three-dimensional structures of biomolecules by using single-molecule diffraction images. *Proc. Natl. Acad. Sci. U.S.A* 98, 6641-6645 (2001).
14. Deng, Z. et al. A close look at proteins: submolecular resolution of two- and three-dimensionally folded cytochrome c at surfaces. *Nano Lett.* 12, 2452-8 (2012).
15. Clemmer, D. E., Hudgins, R. R. & Jarrold, M. F. Naked Protein Conformations: Cytochrome c in the Gas Phase. *J. Am. Chem. Soc.* 117, 10141-10142 (1995).
16. Light-Wahl, K. J., Schwartz, B. L. & Smith, R. D. Observation of the Noncovalent Quaternary Associations of Proteins by Electrospray Ionization Mass Spectrometry. *J. Am. Chem. Soc.* 116, 5271-5278 (1994).
17. Kreuzer, H. J., Nakamura, K., Wierzbicki, A., Fink, H. W. & Schmid, H. Theory of the point-source electron-microscope. *Ultramicroscopy* 45, 381-403 (1992).
18. Latychevskaia, T., Longchamp, J.-N., Escher, C. & Fink, H.-W. Holography and coherent diffraction with low-energy electrons: A route towards structural biology at the single molecule level. *Ultramicroscopy* (2014). doi:10.1016/j.ultramic.2014.11.024
19. Latychevskaia, T. & Fink, H.-W. Practical algorithms for simulation and reconstruction of digital in-line holograms. *Appl. Opt.* 54, 2424 (2015).
20. Heck, A. J. R. Native mass spectrometry: a bridge between interactomics and structural biology. *Nat. Methods* 5, 927-933 (2008).
21. Laganowsky, A., Reading, E., Hopper, J. T. S. & Robinson, C. V. Mass spectrometry of intact membrane protein complexes. *Nat. Protoc.* 8, 639-51 (2013).
22. Mehmood, S., Allison, T. M. & Robinson, C. V. Mass spectrometry of protein complexes: from origins to applications. *Annu. Rev. Phys. Chem.* 66, 453-74 (2015).
23. Longchamp, J.-N., Latychevskaia, T., Escher, C. & Fink, H.-W. Graphene Unit Cell Imaging by Holographic Coherent Diffraction. *Phys. Rev. Lett.* 110, 255501 (2013).
24. Pauly, M. et al. A hydrodynamically optimized nano-electrospray ionization source and vacuum interface. *Analyst* 139, 1856-67 (2014).
25. Gabor, D. A new microscopic principle. *Nature* 161, 777-778 (1948).
26. Gabor, D. Microscopy by reconstructed wave-fronts. *Proc. R. Soc. London Ser. A—Math. Phys. Sci.* 197, 454-487 (1949).
27. Fink, H. W. Point-source for ions and electrons. *Phys. Scr.* 38, 260-263 (1988).
28. Stocker, W., Fink, H. W. & Morin, R. Low-energy electron and ion projection microscopy. *Ultramicroscopy* 31, 379-384 (1989).
29. Kahle, S. et al. The Quantum Magnetism of Individual Manganese-12-Acetate Molecular Magnets Anchored at Surfaces. *Nano Lett.* 12, 518-521 (2012).
30. Kley, C. S. et al. Atomic-scale observation of multiconformational binding and energy level alignment of ruthenium-based photosensitizers on TiO2 anatase. *Nano Lett.* 14, 563-9 (2014).

The invention claimed is:

1. A method of imaging single molecules, comprising:
   a) providing an assembly comprising a carrier substrate having a substrate face with an aperture, the aperture being covered with a receiving layer attached to the substrate face, the receiving layer being substantially transparent for low-energy electrons with a kinetic energy of 5 to 1,000 eV;
   b) depositing single molecules onto said receiving layer by means of soft-landing electrospray ion deposition, whereby a single molecule loaded receiving layer is formed;
   c) acquiring an in-line low-energy electron transmission pattern of said single molecule loaded receiving layer; and
   d) applying a reconstruction procedure to said electron transmission pattern to obtain at least one image of a single molecule on said single molecule loaded receiving layer; wherein
   a) to c) are being conducted under vacuum conditions.

2. The method according to claim 1, wherein b) comprises ionization of single molecules to form single molecular ions, electrostatic extraction and mass filtering of said single molecular ions and electrostatic guidance of mass filtered single molecular ions onto said receiving layer.

3. The method according to claim 1, wherein said single molecules are protein molecules.

4. The method according to claim 1, wherein said receiving layer is a graphene monolayer.

5. The method according to claim 1, wherein said electron transmission pattern is a hologram.

6. The method according to claim 1, wherein said substrate face consists of a platinum metal selected from the group consisting of Pt, Pd and Rh.

7. An apparatus for carrying out the method of claim 1, comprising:
   a) a vacuum chamber containing a carrier substrate having a substrate face with an aperture, the aperture being covered with a receiving layer attached to the substrate face, the receiving layer being substantially transparent for low-energy electrons with a kinetic energy of 5 to 1,000 eV;
   b) means for depositing single molecules onto said receiving layer via soft-landing electrospray ion deposition to form a single molecule loaded receiving layer; and
   c) means for acquiring an in-line low-energy electron transmission pattern of said single molecule loaded receiving layer.

8. The apparatus according to claim 7, further comprising means for applying a reconstruction procedure to said electron transmission pattern to obtain at least one image of a single molecule on said single molecule loaded receiving layer.

9. The apparatus according to claim 8, wherein said means for applying a reconstruction procedure are configured to process a holographic electron transmission pattern.

10. The apparatus according to claim 7, wherein said depositing means comprise means for ionization of single molecules to form single molecular ions, means for electrostatic extraction and mass filtering of said single molecular ions and means for electrostatic guidance of mass filtered single molecular ions onto said receiving layer.

11. The apparatus according to claim 7, wherein said depositing means are configured to deposit single protein molecules.

12. The apparatus according to claim 7, wherein said receiving layer is a graphene monolayer.

13. The apparatus according to claim 7, wherein said substrate face consists of a platinum metal selected from the group consisting of Pt, Pd and Rh.

14. The method according to claim 2, wherein said single molecules are protein molecules.

15. The method according to claim 2, wherein said receiving layer is a graphene monolayer.

16. The method according to claim 2, wherein said electron transmission pattern is a hologram.

17. The method according to claim 6, wherein the platinum metal is Pt.

18. The apparatus according to claim 13, wherein the platinum metal is Pt.

* * * * *